United States Patent [19]
Teass, Jr.

[11] 3,965,414
[45] June 22, 1976

[54] TEMPERATURE COMPENSATED CONDUCTIVITY MEASURING SYSTEM

[76] Inventor: Horace A. Teass, Jr., 73 Remson St., Brooklyn, N.Y. 11201

[22] Filed: May 29, 1975

[21] Appl. No.: 581,816

Related U.S. Application Data

[63] Continuation of Ser. No. 441,953, Feb. 13, 1974, abandoned.

[52] U.S. Cl. .............................. 324/30 R; 324/30 B
[51] Int. Cl.² ......................................... G01N 27/42
[58] Field of Search ............. 324/30 R, 30 B, 62 R, 324/65 R; 204/195 R

[56] References Cited
UNITED STATES PATENTS 3,493,857   2/1970   Silverman ......................... 324/30 B
3,781,911   12/1973  Davidson .......................... 324/65 R

*Primary Examiner*—R. V. Rolinec
*Assistant Examiner*—Michael J. Tokar
*Attorney, Agent, or Firm*—Peck & Peck

[57] ABSTRACT

A system for determining the resistance of an electrolyte into which a conductivity probe is immersed, the system including a thermistor network, a probe or conductivity cell, and amplifiers all of which are so combined that the changes in electrolyte concentrations causing variations in resistance are measured with corrections being made for electrolyte temperature variation. The probe and thermistor networks control the feedback of the amplifier, and the probe and thermistor networks being arranged to adjust the output whereby the signal is in true proportion to conductivity.

6 Claims, 2 Drawing Figures

TEMPERATURE COMPENSATED CONDUCTIVITY MEASURING SYSTEM

This is a continuation of application Ser. No. 441,953 filed Feb. 13, 1974, and now abandoned.

BACKGROUND OF THE INVENTION

There are a substantial number of systems which are known and are now in use for measuring the ionic content of electrolytes. Many of such systems are used in measuring the resistance or conductivity of aqueous solutions. As a general rule, a system of this character is provided with a pair of electrodes which are disposed within the electrolyte forming a probe, and such systems also involve a thermistor combined with the probe and in thermal contact with the electrolyte. Electricity is used to sense the impedance of the fluid path and its current reflects the ionic content to be measured. Different temperatures of the electrolyte materially change the resistance of this fluid path. In many of such systems the thermistor network and the probe's resistance are so combined as to cancel out the changes which result from the temperature variables of the electrolyte. Meters are provided for indicating the resultant ionic content and in many instances, such meters are marked in chemical or other units and such meters are oftentimes laid out in semi-linear or in semi-logarithmic displays. It has been my experience that conventional linear displays are either too expensive or are not temperature compensated and thus are undesirable. The semi-logarithmic displays suffer from the fact that the high ionic values are difficult to read. There are some available linear-digital displays but those of which I am aware have no automatic temperature compensation or have very complex linearization requirements.

SUMMARY OF THE INVENTION

This system provides a novel network which functions to correct the temperature variable aspect of the electrolyte conductivity. In general, the system functions in a novel manner by combining the probe, thermistor network and amplifier together in a manner which will be described in detail hereinafter. It will be apparent, as this description proceeds, that the probe and thermistor network are so designed and arranged as to control the feedback of the amplifier whereby several desirable effects are obtained.

The network of this invention provides a linear display of probe conductance which is accomplished in a novel manner wherein the conductivity probe network and the thermistor network control the feedback of the amplifier. This arrangement of the probe and thermistor networks is such that the display change in reading inverse to the probe's resistance value.

The combination of the various networks in this system measure, but yet correct for the changes in intrinsic electrolyte resistance due to electrolyte temperature change. The probe and thermistor networks and amplifier are so disposed and arranged that the probe and thermistor networks function to adjust the output whereby the gain of the amplifier is controlled. This results in automatic temperature compensation with a linear output.

It is also possible and practical with this system to measure the temperature of the electrolyte by switching in a constant value for the probe. It is evident that this constitutes a novel system whereby the electrolyte temperature may be measured.

DESCRIPTION OF THE PREFERRED EMBODIMENT

Figure 1:
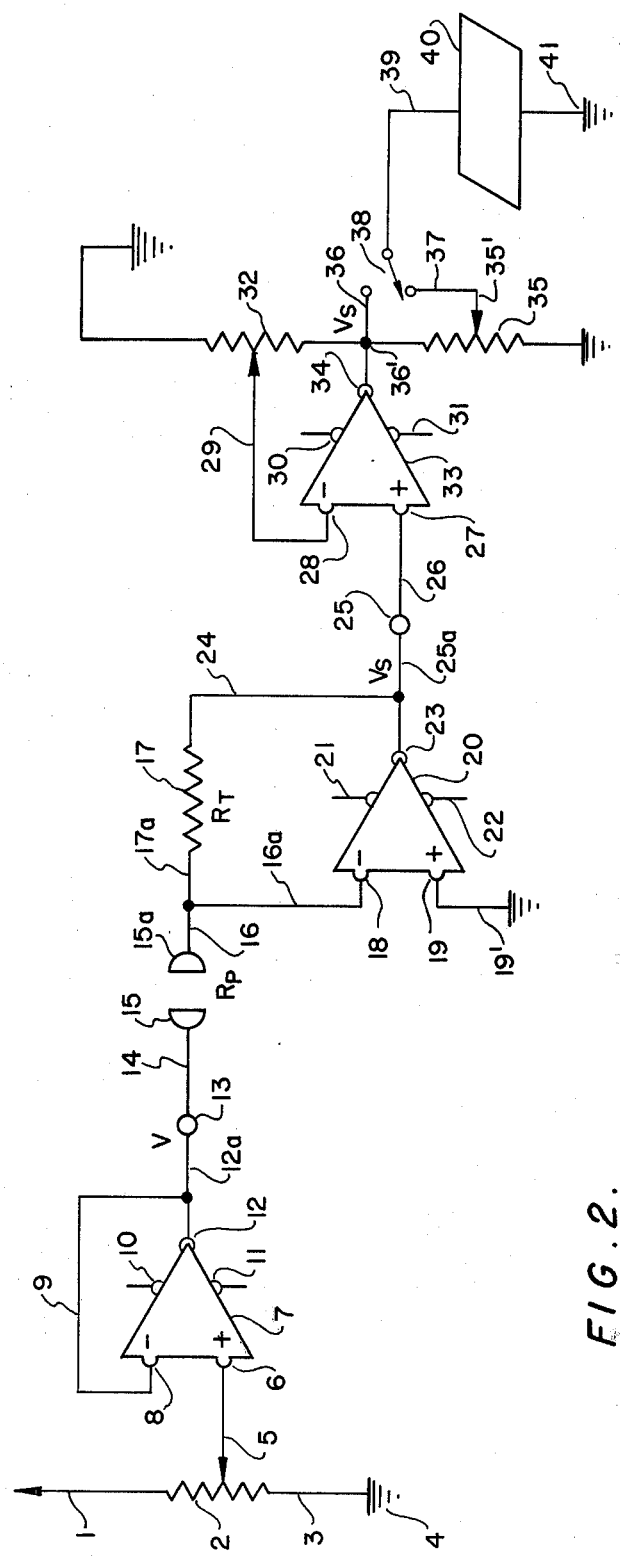
FIG. 1 is a schematic circuit diagram of a preferred temperature compensating conductivity measuring system constructed in accordance with the principles of this invention.
Figure 2:
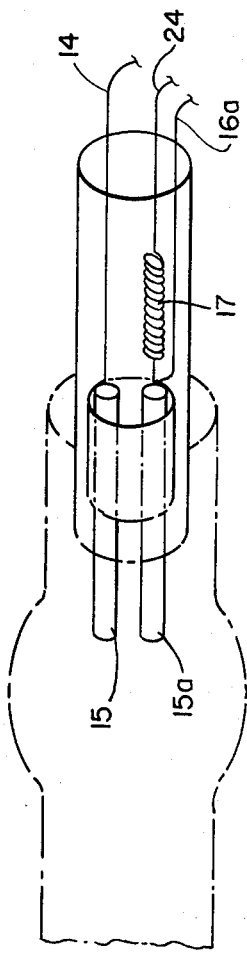
FIG. 2 is a schematic illustration of a typical conductivity cell or probe which may be used in this system.

In a system of this character, the supplied AC power must remain stable and be independent of the changes caused by the variable loading of the probe. If this is not the fact, the cell amplifier system may not operate properly.

The system includes, and I shall describe it, a low impedance source which is novel to the use of a system of this type. A regulated AC source is introduced to the amplifier through a conductor 1 which is connected to one end of a potentiometer 2, the opposite end of the potentiometer being connected to a conductor 3 which is attached to circuit common. A conductor 5 is provided, which is connected to the arm of the potentiometer 2 and this conductor 5 is in electrical connection with the input 6 of amplifier 7. It will thus be apparent that the AC power which is introduced into the amplifier 7 may be varied and consequently the output of amplifier 7 may also be varied. The amplifier 7 has an inverting input 8 which is directly connected to the output of amplifier 7 through conductor 9. Any appropriate DC power source is included in this system to which the power input 10 to amplifier 7 and the power input 11 to amplifier 7 are connected. The voltage output 12 from the amplifier 7 is carried by means of a conductor 12a to a terminal 13. The amplifier acts as a low impedance AC source since the output is sent back into the input. Thus, within reasonable limits, the desirable effect is achieved of supplying AC to the cell probe at a stable voltage. The circuit so far described illustrates the ingenious combination of a voltage follower amplified with a conductivity probe so as to have a stable, adjustable low impedance source which combination when connected as shown results in a constant voltage across the probes.

As I have hereinbefore pointed out, the system which I have devised operates very accurately to correct the temperature variable aspects of the electrolyte's conductivity, and this is specifically accomplished by a particular and specific combination of the thermistor network to control the feedback of the amplifier, which is novel.

The low impedance input terminal 13 with its voltage is connected to a conductor 14 which in turn is electrically connected to the probe 15 of the conductivity cell. The other probe 15a of the conductivity cell is connected to conductor 16. This temperature compensated circuit includes an amplifier 20 which is provided with an inverting input 18 to which the conductor 16 is connected by conductor 16a, the conductor 16 also being connected to the thermistor circuit 17 by conductor 17a. I provide a conductor 24 which is connected by conductor 24a to the output 23 of the amplifier 20, the conductor 24 is also connected to the other end of the thermistor network 17 and output terminal 25 is also electrically connected by means of conductors 25a and 24a to the output 23 of the amplifier. Output voltage will appear on the terminal 25. The noninverting input 19 of amplifier 20 is in electrical connection with circuit common through conductor 19'. Power inputs 21 and 22 of amplifier 20 are electrically connected in any successful and well-known manner to the terminals of a DC power supply.

In order to clarify the operation of this just described cell circuit, it will be helpful if the conductivity probe 15 is considered to be the equivalent to a resistor whose value is Rp and if the thermistor network is considered to have a resistance value Rt. It is to be recognized that the probe 15 is in contact with and immersed in the electrolyte which is being measured and the probe maintains a stable electrical arrangement such that the only reason for Rp to change is that caused by the electrolyte changing its resistance. While the thermistor is in thermal contact with this electrolyte, it is appropriately isolated from electrical contact therewith.

Voltage V on Terminal 13 results in current passing through probe 15 according to the resistance of the electrolyte, which carries to the inverting input terminal 18. A corresponding but inversed voltage Vs then appears on the output 23 of amplifier 20 and this output is in part fed back through thermistor network 17 and again to the inverting input 18 of amplifier 20. As will be understood by one skilled in this discipline, when Rt is large compared to Rp, the output of amplifier 20 will also be large. Thus the ratio between input V and output Vs, or the gain of the inverting amplifier 20, is determined by the ratio of the resistance Rp and Rt. This network has been so designed that when V and Rt remain constant while Rp decreases, the Vs would increase. In other words, as the resistance of the electrolyte decreases, the output Vs will increase. As Rp halves its value, Vs doubles and vice versa. It will, therefore, be apparent that there will be inversed but very accurate relationship between Rp and Vs which will be indicated as increased meter reading with a decreased electrolyte resistance.

It will thus be apparent that this network provides a novel conductivity measuring operation comprising the conductivity probe and the thermistor network which control the feedback of the amplifier resulting in a linear display of probe resistance and also wherein the conductivity probe and the thermistor network control the feedback of the amplifier in such a manner that the display change in reading is inversed to the probe's resistance value.

Further — as has been stated above — the resistance of the electrolyte changes when the temperature of the electrolyte varies, and this network provides an ingenious arrangement which accurately measures and corrects for the changes in the electrolyte resistance caused by temperature changes. The output of the system is adjusted by the combination of the probe and thermistor network values in a novel manner so that the probe and the thermistor network control the gain of the amplifier 20 which results in automatic temperature compensation of the water with a linear output.

Consideration of FIG. 1 indicates an example of the system wherein the input V is held constant. Now if Rt and Rp are changed, the value of these two changes is defined in such a way that the original resistance ratio between the two is preserved and they are connected to the amplifier 20 as shown in the drawing then the output Vs will not change. When Rp changes due to temperature change of the electrolyte then the thermistor changes its Rt in a like rate as that of the electrolyte's Rp. The ratio is preserved and thereby preserves the same Vs. Thus, there is illustrated the conductivity measuring operation comprising the conductivity probe and thermistor network controlling the feedback of the amplifier in such a manner that there is temperature compensation of the reading.

It should be understood that the system involved herein does not require automatic temperature operation and there may be operations where the thermistor network is replaced by a resistor or potentiometer for manual adjustment so that the output Vs may be manually corrected. With this system, the electrolyte temperature may be measured by switching in a constant value for Rp.

This system provides a novel isolating scaler amplifier and digital or linear display. There are several purposes and advantages inherent in this novel isolating scaler amplifier and digital or linear display. For instance, it is not desirable to load down the thermistor cell network 17 so a high input impedance is provided by amplifier 33, also another characteristic of this invention is to provide a system calibrate network. It is also one of my purposes to provide selectable voltage output which allows switching of the display between two or more voltages to show different scales or types of readings.

The output Vs appears on terminal 25 which is connected to conductor 26, the conductor being connected to the noninverting input 27 of amplifier 33. The amplifier 33 is provided with an inverting input 28 which is connected to conductor 29 which is connected to the arm of the potentiometer 32. One side of potentiometer 32 is connected to circuit common through conductor 33, the other side of the potentiometer being connected through conductor 26 to the output 34 of amplifier 33. The inputs 30 and 31 of amplifier 33 are connected to appropriate DC current. Conductor 36 is connected to the output 34 of amplifier 33 and conductor 36 is also connected to a further potentiometer 35 as at 36'. On the opposite end of the potentiometer 35 circuit common is connected. The arm 35' of potentiometer 35 is connected to conductor 37. A switch 38 is included in the circuit and is operable to select a signal from either one of its two positions. It is to be understood that the position of switch 38 which selects potentiometer 35 will have a diminished signal. A conductor 39 is connected to the switch 38 and is also connected to a display indicating device which is diagrammatically illustrated at 40. This may be a meter, a digital meter or other suitable display device. The current of this display device 40 is connected to circuit common through conductor 41.

The configuration of amplifier 33 allows a high degree of isolation and the system calibrate potentiometer 32 allows for full scale adjustment of the digital display device 40. The switch 38 may be used by the operator to select either full output or some other output. A secondary output may be adjusted by a setting of the potentiometer 35. It is within my contemplation to provide the switch 38 with more contacts than are shown so as to provide the operator with greater flexibility. The display device 40 may be connected directly to the output of the amplifier 33.

What is claimed is:

1. An automatic temperature compensated system for measuring and linearly indicating the conductivity of an electrolyte comprising:

a. a regulated AC current source;

b. a first amplifier having input and inverting input leads, an output and a pair of DC power inputs, said input being electrically connected to said regulated AC current source, and said inverting input lead being electrically connected in feedback arrangement to said output;

c. a DC current source connected to said pair of DC power inputs for supplying power to said first amplifier;

d. a conductivity probe having first and second probe elements for immersion into an electrolyte whose conductance is to be measured, said first probe element being electrically connected to said first amplifier output;

e. a second amplifier having input and inverting input leads, an output and a pair of DC power inputs, said input lead being connected to circuit common, said inverting input lead being connected to said second probe element, and said pair of DC power inputs being connected to said DC current source for supplying power to said second amplifier;

f. a thermistor circuit comprising a thermistor having first and second leads, said first lead being connected to said second amplifier inverting input lead and said second lead being connected to said second amplifier output, and said thermistor being in thermal contact with said electrolyte;

g. a third amplifier having input and inverting input leads, an output and a pair of DC power inputs, said input lead being connected to said second amplifier output, said inverting input lead being connected in feedback arrangement to said output and said pair of DC power inputs being connected to said DC current source for supplying power to said third amplifier; and h. measuring means connected between said third amplifier output and circuit common for measuring any electrical output from said third amplifier.

2. An automatic temperature compensated system in accordance with claim 1, and further comprising current varying means electrically connected between said regulated AC current source and said first amplifier input lead for varying the current fed to said first amplifier.

3. An automatic temperature compensated system in accordance with claim 1, wherein said second amplifier comprises an operational amplifier whose output signal is inversely proportional to the resistance of said conductivity probe.

4. An automatic temperature compensated system in accordance with claim 1, and further comprising a potentiometer having first and second leads and a slidable arm output, said first lead being connected to said third amplifier output, said second lead being connected to circuit common and said slidable arm output being connected to said third amplifier inverting input lead, whereby a variable impedance feedback path is formed for said third amplifier permitting the magnitude of the output of said third amplifier to be selectably varied, and said measuring means comprises a meter having a plurality of selectable range-scales.

5. An automatic temperature compensated system in accordance with claim 1, and further comprising a potentiometer having first and second leads and a slidable arm output, said first lead being connected to said third amplifier output and said second lead being connected to circuit common; a multipole switch comprising first and second terminals and a switch arm selectably movable between said first and second terminals, said first terminal being connected to said third amplifier output and said second terminal being connected to said potentiometer slidable arm; and said measuring means comprises a meter having a plurality of selectable range-scales, said meter being electrically connected between said switch arm and circuit common to measure any output from said third amplifier.

6. An automatic temperature compensated system in accordance with claim 4, and further comprising a second potentiometer having first and second leads and a slidable arm output, said first lead being connected to said third amplifier output and said second lead being connected to circuit common; a multipole switch comprising first and second terminals and a switch arm selectably movable between said first and second terminals, said first terminal being connected to said third amplifier output, said second terminal being connected to said second potentiometer slidable arm output; and said measuring means comprises a meter having a plurality of selectable range-scales, said meter being electrically connected between said switch arm and circuit common to measure any output from said third amplifier.

* * * * *